United States Patent
Miyoshi et al.

(10) Patent No.: US 12,318,630 B2
(45) Date of Patent: Jun. 3, 2025

(54) TREATMENT PLANNING SYSTEM, TREATMENT PLAN CREATION METHOD, AND COMPUTER PROGRAM

(71) Applicant: Hitachi, Ltd., Tokyo (JP)

(72) Inventors: Takuto Miyoshi, Tokyo (JP); Shinichirou Fujitaka, Tokyo (JP); Taisuke Takayanagi, Tokyo (JP)

(73) Assignee: HITACHI, LTD., Tokyo (JP)

( * ) Notice: Subject to any disclaimer, the term of this patent is extended or adjusted under 35 U.S.C. 154(b) by 351 days.

(21) Appl. No.: 17/724,582

(22) Filed: Apr. 20, 2022

(65) Prior Publication Data

US 2022/0379138 A1 Dec. 1, 2022

(30) Foreign Application Priority Data

May 28, 2021 (JP) ................. 2021-090707

(51) Int. Cl.
*A61N 5/10* (2006.01)
*G16H 20/40* (2018.01)
*G16H 30/40* (2018.01)

(52) U.S. Cl.
CPC .......... *A61N 5/1031* (2013.01); *A61N 5/1039* (2013.01); *A61N 5/1077* (2013.01); *G16H 20/40* (2018.01); *G16H 30/40* (2018.01)

(58) Field of Classification Search
None
See application file for complete search history.

(56) References Cited

U.S. PATENT DOCUMENTS

2017/0304651 A1\* 10/2017 Takayanagi .......... A61N 5/1043

FOREIGN PATENT DOCUMENTS

JP 2020-146334 A 9/2020

\* cited by examiner

*Primary Examiner* — Hoon K Song
(74) *Attorney, Agent, or Firm* — MATTINGLY & MALUR, PC

(57) ABSTRACT

A correlation between a CT value and a water equivalent thickness ratio distribution for each patient can be corrected without increasing a treatment time, and more accurate treatment can be realized. A treatment planning system 112 which generates a treatment plan for irradiating an irradiation target with a particle beam calculates a correction amount of a water equivalent thickness ratio of a first treatment plan created in advance, calculates a water equivalent thickness ratio distribution based on the correction amount and the first treatment plan, and creates a second treatment plan from the water equivalent thickness distribution.

10 Claims, 11 Drawing Sheets

TREATMENT PLANNING SYSTEM, TREATMENT PLAN CREATION METHOD, AND COMPUTER PROGRAM

CROSS-REFERENCE TO RELATED APPLICATION

The present application claims priority from Japanese application JP2021-090707, filed on May 28, 2021, the contents of which is hereby incorporated by reference into this application.

TECHNICAL FIELD

The present invention relates to a treatment planning system, a treatment plan creation method, and a computer program.

BACKGROUND ART

The present invention preferably relates to a particle beam therapy system, a range measurement device of a particle beam, and a treatment planning system for performing cancer treatment by irradiating an affected part of cancer with a particle beam.

A particle beam such as a proton beam or a carbon beam applies a large dose immediately before stopping in a patient body. Due to the use of this large dose, that is, a so-called Bragg peak, it is easy to form a dose distribution matching a tumor shape as compared with X-ray treatment, and it is expected that radiation treatment with high accuracy is realized.

In particle beam therapy, a range (a position of the Bragg peak) for each particle beam is estimated from a distribution of a water equivalent thickness ratio (a ratio of a thickness of water and a thickness of a local medium that cause the same energy loss) in the patient body, and a dose distribution is calculated. An irradiation position and an irradiation amount of each beam for applying a target dose to each region in the patient body are determined based on the dose distribution. This irradiation condition is referred to as a prescription, and a procedure for determining the condition is referred to as a treatment plan.

However, it is known that an error of several percentages occurs between a range obtained by dose calculation and a measured range. A main cause of the error is a change in an internal structure and a difference in the water equivalent thickness ratio for each patient.

The distribution of the water equivalent thickness ratio used for the calculation of the range is calculated by converting an X-ray computed tomography (hereinafter, referred to as CT) image of a patient captured in advance by a conversion table of a CT value and a water equivalent thickness ratio created by using a phantom. A first main cause of the range error is that the water equivalent thickness ratio distribution changes due to a variation in the internal structure at the time of capturing the CT image and irradiation with the particle beam. On the other hand, since a correlation between the CT value and the water equivalent thickness ratio varies depending on the patient, even though there is no variation in the internal structure, the water equivalent thickness ratio distribution converted from the CT value has an error from an actual distribution. This is a second main cause of the error.

In a general treatment plan, a region obtained by adding a blank (hereinafter, referred to as a margin) to a tumor in order to add the range error is set as a target volume. However, when the margin is large, it is difficult to apply a high dose to the tumor surrounded by critical organs. Accordingly, in order to expand an application range of the particle beam therapy, it is necessary to improve treatment accuracy by suppressing the range error, and it is necessary to reduce the margin.

The variation in the internal structure which is one of the main causes of the range error can be reflected in the treatment plan by daily observing the internal structure by CT or magnetic resonance imaging. On the other hand, in order to suppress an error due to patient dependence of the water equivalent thickness ratio, it is necessary to acquire the distribution of the water equivalent thickness ratio for each patient.

As one of methods for acquiring the distribution of the water equivalent thickness ratio, the measurement of the water equivalent thickness ratio distribution by proton beam CT has been studied. In the proton beam CT, the water equivalent thickness ratio distribution in the patient body is directly measured by three-dimensionally emitting a proton beam having energy higher than at the time of treatment and measuring a transmission line.

PTL 1 discloses a particle beam therapy system including a residual range measurement device that can emit a proton beam and a helium beam as charged particle beams and measures energy of the proton beam that has passed through a patient and a particle beam CT image generation device that obtains a stopping power ratio distribution for the proton beam of the patient measured by the residual range measurement device and calculates the stopping power ratio distribution for the helium beam based on the obtained stopping power ratio distribution.

CITATION LIST

Patent Literature

PTL 1: JP 2020-146334 A

SUMMARY OF INVENTION

Technical Problem

The accuracy of the particle beam therapy is improved by acquiring the distribution of the water equivalent thickness ratio for each patient. As disclosed in PTL 1, since the proton beam CT which is one of the methods for measuring the water equivalent thickness ratio uses the same line type as that of the treatment, the measurement accuracy of the water equivalent thickness ratio for the treatment beam is high. Since the irradiation is performed independently of the treatment, there is a high degree of freedom in selecting which part of the body is measured for the water equivalent thickness ratio and how much a resolution is set.

However, a large-scaled acceleration device is required to extract a proton beam having higher energy than energy used in the treatment. Since the proton beam CT is added to a treatment process, an increase in treatment time is also assumed.

As described above, the proton beam CT is a high-performance measurement method of the water equivalent thickness ratio, but there are some problems from a clinical viewpoint. In order to realize the particle beam therapy with high accuracy, low cost, and high throughput, it is necessary to correct a correlation between the CT value and the water equivalent thickness ratio for each patient without increasing the treatment time by adding the measurement process other than the treatment.

The present invention has been made in view of the above circumstances, and an object of the present invention is to provide a treatment planning system, a treatment plan creation method, and a computer program capable of correcting a correlation between a CT value and a water equivalent thickness ratio distribution for each patient without increasing a treatment time and realizing more accurate treatment.

Solution to Problem

In order to solve the problems, a treatment planning system according to one aspect of the present invention is a treatment planning system which generates a treatment plan for irradiating an irradiation target with a particle beam. The treatment planning system calculates a correction amount of a water equivalent thickness ratio of a first treatment plan created in advance, calculates a water equivalent thickness ratio distribution based on the correction amount and the first treatment plan, and creates a second treatment plan from the water equivalent thickness ratio distribution.

Advantageous Effects of Invention

According to the present invention, the correlation between the CT value and the water equivalent thickness ratio distribution for each patient can be corrected without increasing the treatment time, and more accurate treatment can be realized.

DESCRIPTION OF EMBODIMENTS

Figure 1:
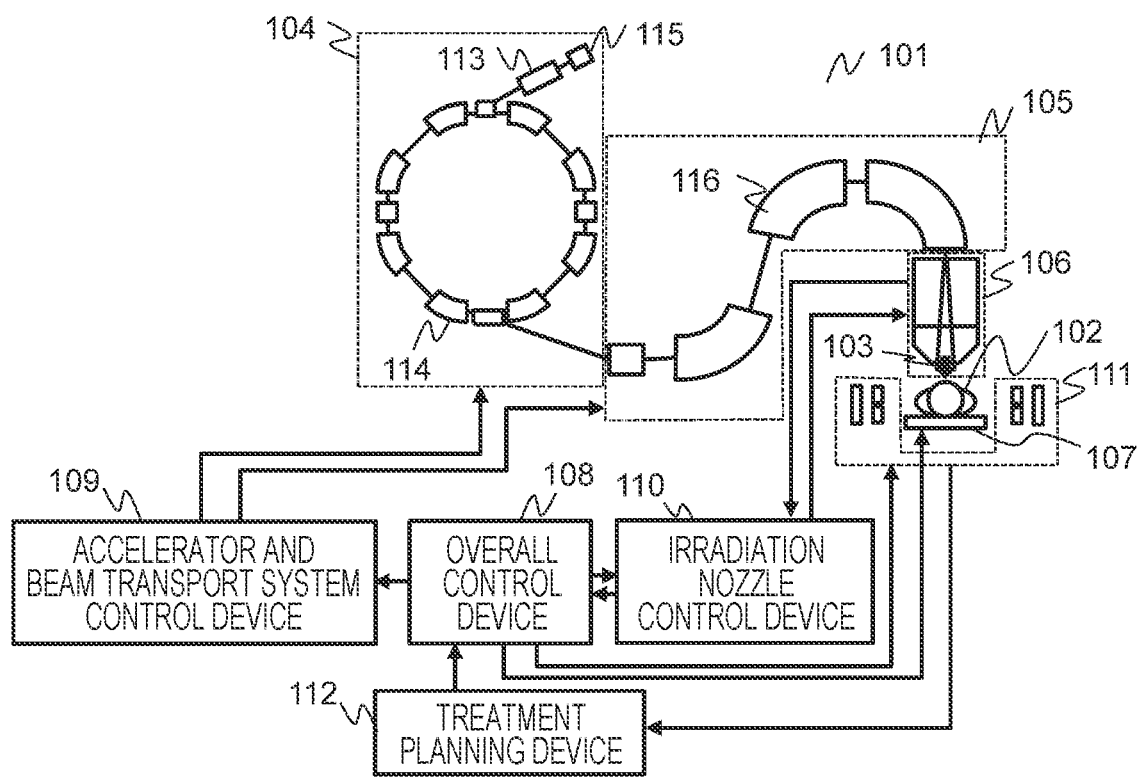
FIG. 1 is a diagram illustrating an overall configuration of a particle beam therapy system according to a first embodiment.

Hereinafter, embodiments of the present invention will be described with reference to the drawings. The following description and drawings are examples for describing the present invention, and are appropriately omitted and simplified in order to clarify the description. The present invention can be implemented in other various forms. Unless otherwise limited, each component may be singular or plural.

In the embodiments, components having the same function are assigned by the same reference sign, and redundant description thereof will be omitted unless particularly necessary.

Positions, sizes, shapes, and ranges of components illustrated in the drawings may not necessarily represent actual positions, sizes, shapes, and ranges in order to facilitate understanding of the invention. Thus, the present invention is not necessarily limited to the positions, sizes, shapes, and ranges disclosed in the drawings.

When there is a plurality of components having the same or similar functions, the plurality of components will be described with different subscripts given to the same reference signs. In this case, when there is no need to distinguish between the plurality of components, the plurality of components will be described with the subscripts omitted.

A particle beam therapy system including a treatment planning system of the present embodiment has the following configuration as an example.

That is, an example of a particle beam therapy system including a treatment planning system according to the present embodiment is a particle beam therapy system which irradiates an irradiation target with a particle beam. The particle beam therapy system includes an irradiation device which irradiates the irradiation target with the particle beam accelerated by an accelerator, a range measurement device which is disposed on a side surface of the irradiation target, is synchronized with the irradiation device, and measures measured range of the particle beam, and a treatment planning system which executes calculation and correction of a water equivalent thickness ratio distribution and creation of a prescription. The treatment planning system has a function of dividing a region of the X-ray CT image of the patient, a water equivalent thickness ratio calculation program for calculating a target volume and a water equivalent thickness ratio distribution based on a water equivalent thickness ratio correction result until a previous treatment, a prescription creation program for creating a prescription of the particle beam from the water equivalent thickness ratio distribution, and a water equivalent thickness ratio correction program for determining a water equivalent thickness ratio correction amount from information such as the measured range and the prescription.

According to the present embodiment, since the correction amount of the water equivalent thickness ratio can be estimated from the measured range of the treatment particle beam, an increase in size of an acceleration device and an increase in treatment time do not occur. It is possible to perform water equivalent thickness ratio correction with high accuracy from limited range error information by using a method for dividing a CT image into regions and determining the water equivalent thickness ratio correction amount for each region. Correction accuracy can be improved by accumulating range error information used for the water equivalent thickness ratio correction for each treatment cycle, and the improvement in the accuracy can be reflected in a treatment plan by reducing a margin.

A radiation treatment planning system (hereinafter, simply referred to as a "treatment planning system") according to an embodiment will be described with reference to FIGS. 1 to 11. In the present embodiment, although a treatment planning system that drafts a treatment plan of proton beam treatment by a scanning irradiation method which is a type of radiation treatment will be described, the present invention is also applicable to a treatment planning system that drafts a treatment plan of proton beam treatment by a scatterer irradiation method or heavy particle beam therapy using a carbon beam or the like. The present invention is also applicable to a treatment planning system for X-ray treatment.

First Embodiment

Hereinafter, a treatment planning system of the present embodiment will be described with reference to FIGS. 1 to 10. A configuration of a particle beam therapy system including a treatment planning system of the present embodiment will be described in the first half with reference to FIGS. 1 to 5, and an operation procedure of the system according to the first embodiment will be described in the latter half with reference to FIGS. 6 to 10.

First, an overall configuration of the particle beam therapy system will be described with reference to FIG. 1. FIG. 1 is a diagram illustrating an overall configuration of a particle beam therapy system of the present embodiment.

A particle beam therapy system 101 of the present embodiment employs spot scanning irradiation. The spot scanning irradiation is a method for forming a target dose distribution by irradiating each minute irradiation region (hereinafter, referred to as a spot) in an irradiation target 102 with a pencil beam (small spread particle beam, hereinafter, referred to as a beam 103).

The particle beam therapy system 101 is a system for irradiating the irradiation target 102 with the beam 103, and includes an accelerator system 104, a beam transport system 105, an irradiation nozzle 106, a treatment stand 107, an overall control device 108, an accelerator and beam transport system control device 109, an irradiation nozzle control device 110, a range measurement device 111, and a treatment planning system 112, as illustrated in FIG. 1.

The accelerator system 104 is a device that generates and accelerates the beam 103. In FIG. 1, examples of an injector 113, a synchrotron accelerator 114, and an ion source 115 are illustrated as accelerators, but may be a cyclotron accelerator or a synchrocyclotron accelerator.

The beam transport system 105 is a device group that transports the beam 103 accelerated by the accelerator 104 to the irradiation nozzle 106 that irradiates the irradiation target 102 with the beam 103, and connects the accelerator 104 and the irradiation nozzle 106. The beam 103 accelerated to required energy by the accelerator 104 is transported to the irradiation nozzle 106 while being bent by a magnetic field in vacuum by bending magnets 116 arranged in the beam transport system 105. The beam transport system 105 has a rotary gantry, but may be a fixed irradiation port.

The irradiation nozzle 106 is a device that adjusts the beam 103 transported from the beam transport system 105 and irradiates the irradiation target 102 with the beam. A detailed configuration of the irradiation nozzle 106 will be described later with reference to FIG. 2.

Figure 3:
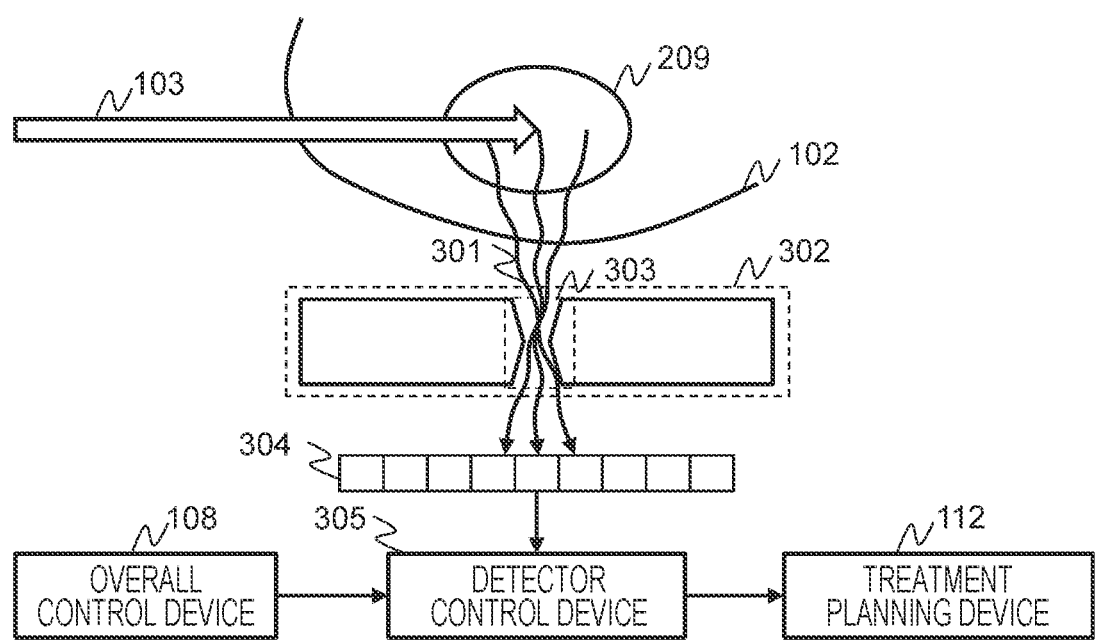
FIG. 3 is a diagram illustrating an outline of a range measurement device using a prompt gamma ray in the particle beam therapy system according to the first embodiment.

The range measurement device 111 is a device that measures a range of the beam 103 in the irradiation target 102 and outputs the range to the treatment planning system 112. As illustrated in FIG. 3, in the present embodiment, although a prompt gamma ray measurement device is illustrated as an example of the range measurement device, any device that can measure the range in the irradiation target 102 for each beam 103 may be used, and an ultrasonic measurement device and an annihilation gamma ray measurement device may be used. A detailed configuration of the range measurement device 111 and a method for determining the range will be described later with reference to FIGS. 3 and 4.

Again, in FIG. 1, the treatment planning system 112 implements the treatment plan to create a prescription, and further transports the prescription to the overall control device 108, and also corrects a distribution of water equivalent thickness s ratio from the range or the like measured by the range measurement device 111. A detailed configuration and an operation of the treatment planning system 112 will be described later with reference to FIG. 5.

The accelerator and beam transport system control device 109 controls an operation of each device constituting the accelerator system 104 and the beam transport system 105.

The irradiation nozzle control device 110 controls an operation of each device constituting the irradiation nozzle 106.

The overall control device 108 is connected to the treatment planning system 112, the accelerator and beam transport system control device 109, the irradiation nozzle control device 110, the range measurement device 111, and the treatment stand 107, and controls an operation of each device.

The overall control device 108, the accelerator and beam transport system control device 109, the irradiation nozzle control device 110, the range measurement device 111, and the treatment planning system 112 include a central processing unit (CPU) and a memory connected to the CPU.

Control processing of an operation to be executed may be integrated into one program, may be divided into a plurality of programs, or may be a combination thereof.

Some or all of the programs retained in the devices may be implemented by dedicated hardware or may be modularized. Various programs may be installed in each device by a program distribution server or an external storage medium, or an existing device may be updated.

Each device may be an independent device and connected by a wired or wireless network, or two or more devices may be integrated.

The treatment stand 107 is a bed on which a patient as the irradiation target 102 is placed. The treatment stand 107 can move in directions of three orthogonal axes based on an instruction from the overall control device 108, and can further move in a so-called six-axis direction that rotates about each axis. By the movement and rotation thereof, a position of the irradiation target 102 can be moved to a desired position.

Figure 2:
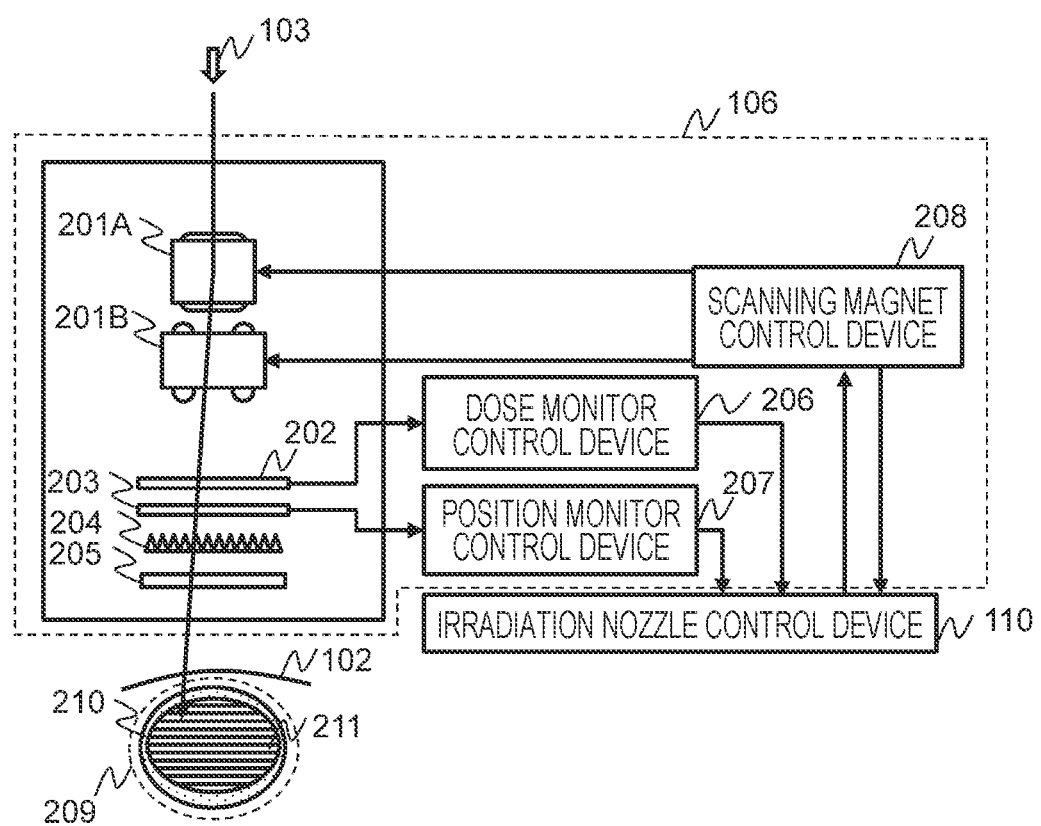
FIG. 2 is a diagram illustrating a configuration of an irradiation nozzle of the particle beam therapy system according to the first embodiment.

Next, a detailed configuration of the irradiation nozzle 106 will be described with reference to FIG. 2. FIG. 2 is a diagram illustrating a configuration of the irradiation nozzle 106.

In the irradiation nozzle 106, scanning magnets 201A and 201B, a dose monitor 202, a position monitor 203, a ridge filter 204, and a range shifter 205 are arranged. The irradiation nozzle control device 110 is connected to a dose monitor control device 206, a position monitor control device 207, and a scanning magnet control device 208.

The scanning magnets 201A and 201B scan a plane perpendicular to a passing direction of the beam 103 with the beam 103. A target volume 209 in the irradiation target 102 is irradiated with the beam 103 scanned by the scanning magnets 201A and 201B. When a patient with cancer is treated, the irradiation target 102 represents the patient, and the target volume 209 represents tumor 211 or the like to which a margin 210 is added.

The dose monitor 202 is a monitor for collecting electrons generated by the passage of the beam 103 in order to measure the dose of the beam 103 with which each spot position is irradiated, and a detection signal is input to the dose monitor control device 206. The dose monitor control device 206 calculates the irradiation amount with which each spot position is irradiated based on the detection signal input from the dose monitor 202, and outputs the calculated irradiation amount to the irradiation nozzle control device 110.

The position monitor 203 is a monitor for collecting electrons generated by the passage of the beam 103 in order to measure each spot position. A detection signal of the position monitor 203 (a pulse signal obtained by collecting the electrons) is input to the position monitor control device 207. The position monitor control device 207 counts the dose at each spot position based on the detection signal 203, and outputs the input from the position monitor calculated count value to the irradiation nozzle control device 110.

The ridge filter 204 can be used when it is necessary to thicken a Bragg peak. The range shifter 205 can be inserted when an arrival position of the beam 103 is adjusted.

In the spot scanning irradiation, the irradiation nozzle control device 110 obtains a passing position of the beam 103 based on the signal input to the position monitor control device 207, performs the spot position from data of the obtained passing position, and confirms an irradiation position of the beam 103. When the irradiation amount input to the dose monitor control device 206 reaches a target dose, the irradiation nozzle control device 110 subsequently scans a spot with the beam 103 via the scanning magnet control device 208. When all spot groups (referred to as layers) with the same energy are irradiated, the irradiation nozzle control device 110 transmits a signal to the overall control device 108. When a signal indicating that the irradiation of the layers is expired is received from the irradiation nozzle control device 110, the overall control device 108 sends a command to the accelerator and beam transport system control device 109 to change the energy of the beam 103 and start the irradiation of the next layer.

Next, details of the range measurement device 111 will be described with reference to FIG. 3. In the present embodiment, the range measurement device using the prompt gamma rays is exemplified as an example of the range measurement device, and FIG. 3 is a diagram illustrating an outline thereof.

Prompt gamma rays 301 are generated by an interaction between the beam 103 with which the irradiation target 102 is irradiated and the irradiation target 102.

A collimator 302 is installed on a side surface of the target volume 209 viewed from a traveling direction of the beam 103. The collimator 302 shields rays other than the prompt gamma rays 301 passing through a slit 303. For example, a tungsten or lead block is used as a material of the collimator. Although FIG. 3 illustrates a case where inner walls of the slit 303 of the collimator 302 are triangular, a shape of the slit 303 may be formed, for example, such that inner walls are parallel to each other.

An array type detector 304 detects the prompt gamma rays 301 that have passed through the slit 303. Arrays are arranged in the beam traveling direction, and the detection positions of the prompt gamma rays 301 can be obtained by distinguishing between signals for the arrays. A semiconductor, a combined detector of a phosphor and a photodetector, or the like is used as the array type detector 304.

A detector control device 305 is connected to the array type detector 304, the overall control device 108, and the treatment planning system 112. The detector control device 305 receives information on the beam 103 being irradiated from the overall control device 108 and receives a signal from the array type detector 304 for each beam 103. Subsequently, the detector control device 305 determines the range from the detected signal and transmits the range to the treatment planning system 112.

Figure 4:
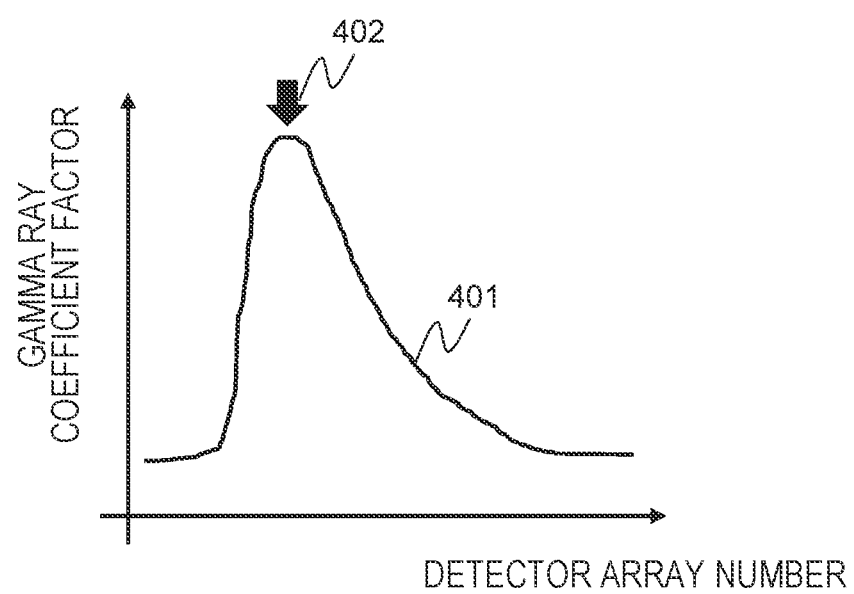
FIG. 4 is a diagram illustrating a signal acquired by range measurement using the prompt gamma ray in the particle beam therapy system according to the first embodiment.

FIG. 4 illustrates an example of the detection signal of the array type detector 304. Since the number of prompt gamma rays 301 generated from the irradiation target 102 is correlated with the applied dose, the number of prompt gamma rays rapidly increases near the range. Accordingly, when the arrays of the array type detector 304 are numbered in an arrangement order in a real space and are plotted on a horizontal axis and coefficient rates for the arrays are plotted on a vertical axis, a shape corresponding to the Bragg peak such as a detection signal 401 is observed.

However, the distribution of the prompt gamma rays 301 detected by the array type detector 304 is inverted around a position of the slit 303 as compared with the distribution of the prompt gamma rays 301 in the target volume 209. The detector control device 305 determines a measured range 402 from a position of a peak of the detection signal 401.

FIG. 3 illustrates a case where the collimator 302 is fixed and the distribution of the prompt gamma rays 301 is measured, but the measurement may be performed while the collimator 302 is translated in the traveling direction of the beam 103.

Figure 5:
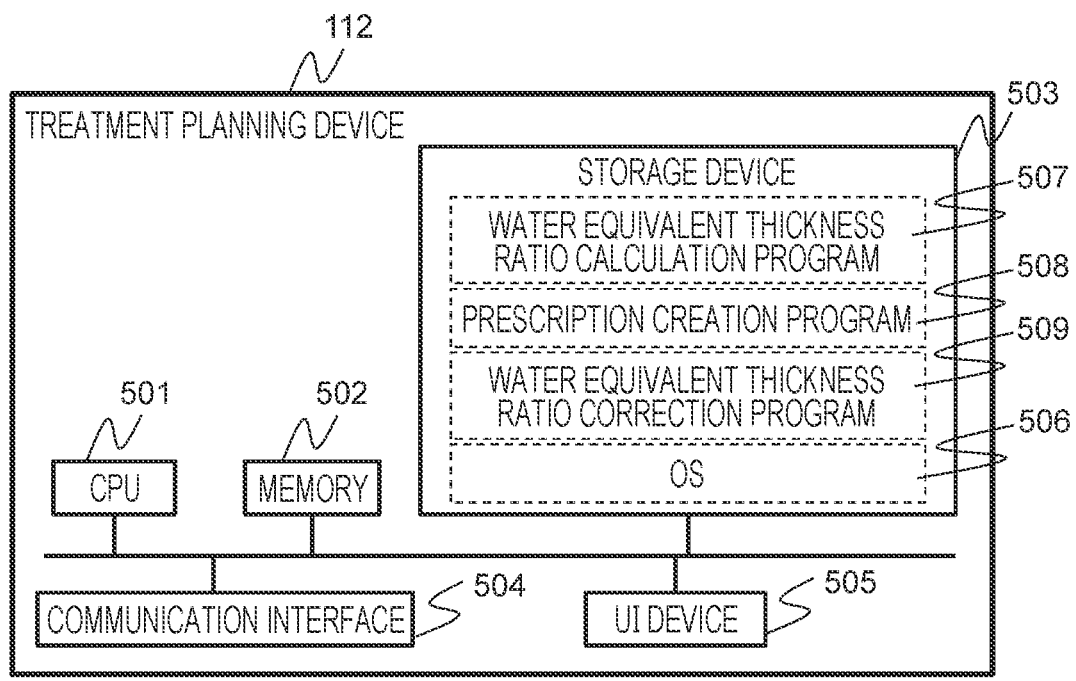
FIG. 5 is a diagram illustrating a configuration of a treatment planning system in the particle beam therapy system according to the first embodiment.

Next, the detailed configuration of the treatment planning system 112 will be described with reference to FIG. 5. FIG. 5 is a configuration diagram of the treatment planning system 112.

The treatment planning system 112 is a computer system including, for example, a CPU 501, a memory 502, a storage device 503, a communication interface device 504, and a user interface (UI) device 505.

The storage device 503 includes, for example, a flash memory device, a hard disk drive (HDD), and the like, and stores computer programs such as an operating system (OS) 506, a water equivalent thickness ratio calculation program 507, a prescription creation program 508, and a water equivalent thickness ratio correction program 509. After the start of treatment, information used for water equivalent thickness ratio correction and treatment planning is stored. Details of the stored information will be described later in the description of the operation procedure.

The CPU 501 reads various programs (507, 508, and 509) stored in the storage device 503 into the memory 502 and executes the programs, and thus, functions (water equivalent thickness ratio calculation, prescription creation, and water equivalent thickness ratio correction) as the treatment planning system 112 are realized. Here, although the CPU 501 is used as a representative of a calculation element, a graphic processing unit (GPU), a field-programmable gate array (FPGA), or the like may be used as the calculation element in addition to the CPU 501.

The communication interface device 504 is a device for communicating with the devices (overall control device 108 and range measurement device 111) of the particle beam therapy system 101.

The UI device 505 is a device that exchanges information with a user (hereinafter, referred to as a doctor) who uses the treatment planning system 112. The UI device 505 includes an information output device and an information input device. Examples of the information output device include a display, a printer, and a voice synthesizer. Examples of the information input device include a keyboard, a pointing device, a touch panel, and a voice recognition device. For example, the dose distribution calculation result of the prescription creation program 508 is displayed on the display.

The configuration of the particle beam therapy system 101 and the details of each device are as described above. Hereinafter, the operation procedure of the system according to the first embodiment will be described.

Figure 6:
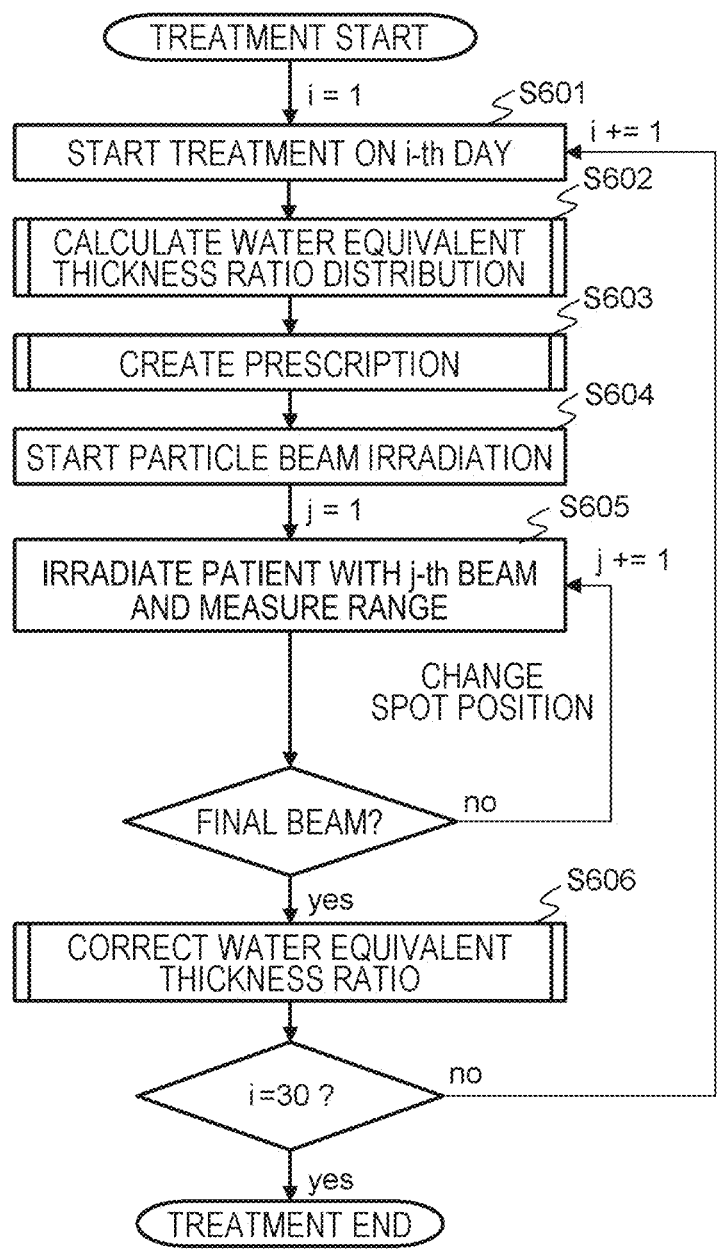
FIG. 6 is a diagram illustrating a flowchart of the entire particle beam therapy by the particle beam therapy system according to the first embodiment.

A treatment procedure by the particle beam therapy system 101 will be described mainly with reference to FIG. 6. However, FIGS. 7 to 10 are appropriately used to supplement the detailed procedure. FIG. 6 is a diagram illustrating a flowchart of the entire particle beam therapy.

In general, in the particle beam therapy, fractionated irradiation in which a target dose is applied several times is performed. This is to prevent normal tissues from being damaged by application of a high dose at a time. In the present embodiment, although a target dose of 60 Gy is divided into 2 Gy per day and is irradiated for 30 days, when the number of times of division is two or more, the effect of the present invention is not lost even though the number of times of division and the irradiation amount are changed. A division unit may not be one day, and daily treatment may be subdivided into multiple treatments.

Since the treatment procedure is different between the first day, the second day and the subsequent days, and the thirtieth day, the description will be made in chronological order from the first day.

When the treatment on the first day is started (step S601), first, the water equivalent thickness ratio calculation program 507 of the treatment planning system 112 calculates a water equivalent thickness ratio distribution (step S602).

Figure 7:
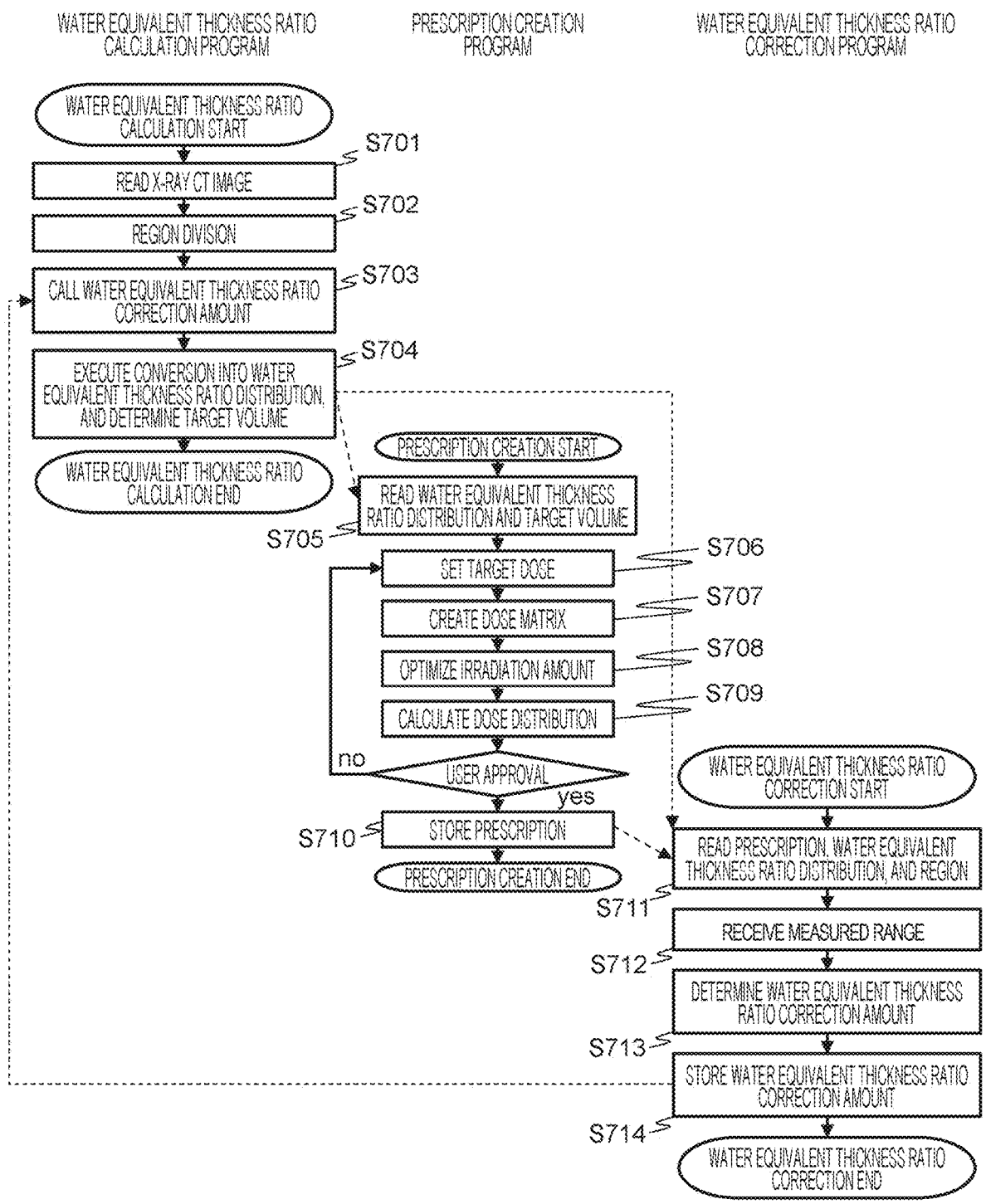
FIG. 7 is a diagram illustrating details of a flowchart of a step in which the treatment planning system operates in the particle beam therapy by the particle beam therapy system according to the first embodiment.

Details of the water equivalent thickness ratio distribution calculation will be described with reference to FIG. 7. FIG. 7 is a flowchart illustrating details of the operation of each program of the treatment planning system 112.

The water equivalent thickness ratio calculation program 507 first reads an X-ray CT image of a periphery of an affected part of the patient captured by an X-ray CT apparatus outside the particle beam therapy system 101 (step S701). The X-ray CT apparatus may transmit a CT image to the treatment planning system 112 immediately after capturing, or the X-ray CT apparatus may store the CT image in the X-ray CT apparatus itself or an external storage device and may read the CT image when the treatment planning system 112 starts the water equivalent thickness ratio calculation (step S602).

Subsequently, the water equivalent thickness ratio calculation program 507 divides a region of the CT image (step S702). However, since region division information is not necessary for the water equivalent thickness ratio calculation on the first day, the region division may be executed in any step up to the water equivalent thickness ratio correction (step S711) executed after the particle beam irradiation.

Figure 8:
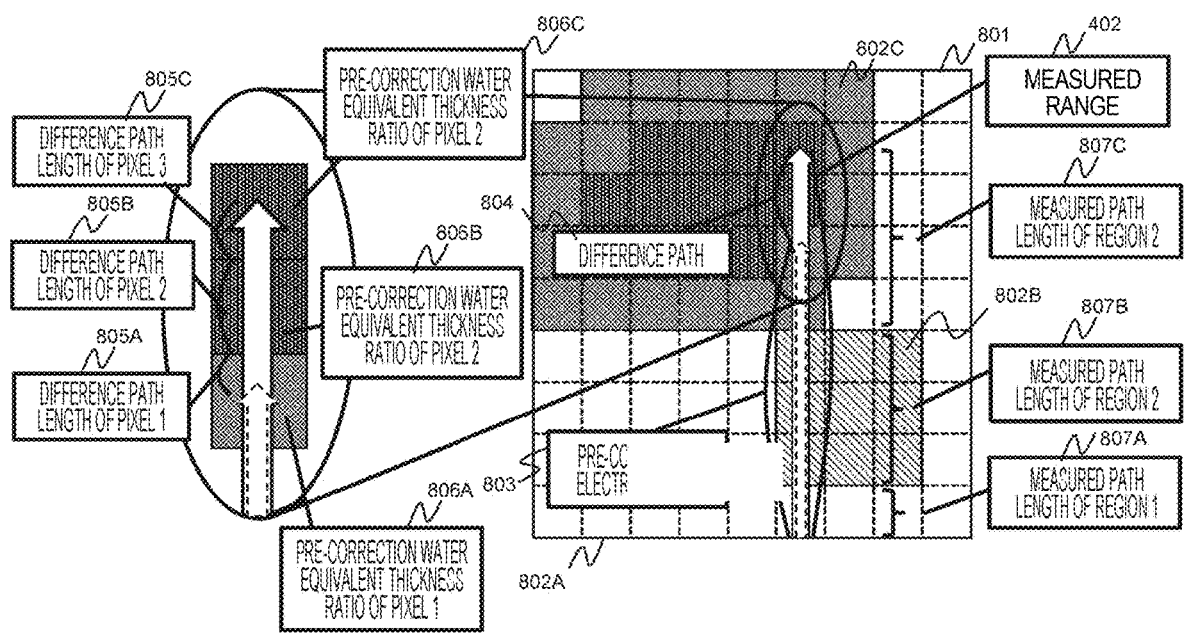
FIG. 8 is a diagram for describing an input amount used for dividing a region of an X-ray CT image of a patient and a water equivalent thickness ratio correction amount in a treatment plan creation operation by the treatment planning system according to the first embodiment.

The region division of the CT image will be supplemented with reference to FIG. 8. In FIG. 8, each pixel of an X-ray CT image 801 is represented by a square, and a difference in CT value is indicated by density of color of the square.

The division of a region 802 is determined based on the X-ray CT image 801. When the division of the region 802 is determined, the X-ray CT image 801 may be displayed on the UI device 505 and may be divided for each type of a body tissue by the doctor, or a program for integrating pixels having close CT values into one region may be incorporated into the treatment planning system 112 and may be automatically implemented.

In FIG. 8, a boundary of the region 802 is indicated by a thick line, and is divided into three regions (802A, 802B, and 802C) of a region 1 to a region 3. The number of regions 802 is not limited to three and can be randomly set. However, when the number of regions 802 is larger than the number of pieces of information on the measured range 402, it is assumed that the water equivalent thickness ratio correction amount determined by a method to be described later does not apply well or the determination processing of the water equivalent thickness ratio correction amount is not normally operated.

Referring back to FIG. 7, subsequently, the water equivalent thickness ratio calculation program 507 executes conversion of the X-ray CT image 801 into the water equivalent thickness ratio distribution and determination of the target volume 209 (step S704). Since the water equivalent thickness ratio correction is not executed at a point in time of step S704 in the treatment on the first day, the call of the water equivalent thickness ratio correction amount (step S703) is skipped.

Figure 9:
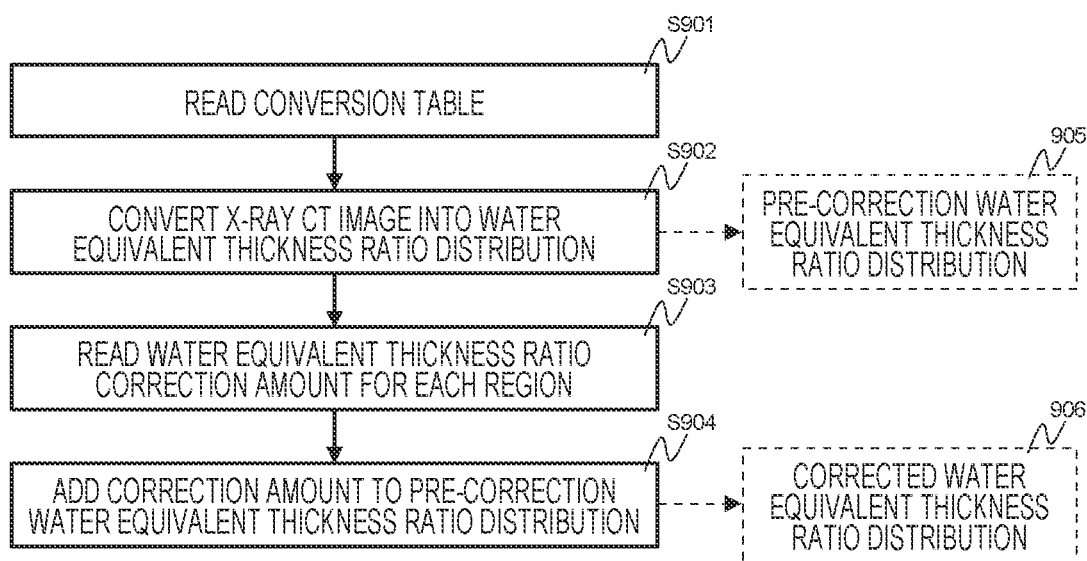
FIG. 9 is a diagram illustrating a flowchart of water equivalent thickness ratio distribution calculation of a water equivalent thickness ratio calculation program in a treatment plan creation operation by the treatment planning system according to the first embodiment.

A conversion flow of the water equivalent thickness ratio distribution will be described with reference to FIG. 9. On the first day, of two types of water equivalent thickness ratio distributions (pre-correction water equivalent thickness ratio distribution 905 and corrected water equivalent thickness ratio distribution 906) illustrated in FIG. 9, only the pre-correction water equivalent thickness ratio distribution 905 is created. A conversion table of the CT value and the water equivalent thickness ratio stored in advance in the treatment planning system 112 is read (step S901), and the pre-correction water equivalent thickness ratio distribution 905 is calculated by converting the X-ray CT image 801 by using the conversion table (step S902). Here, the conversion table is created in advance by measurement using a phantom or the like, and is constant regardless of the patient. Assuming that a file in which a relational expression between the CT value and the water equivalent thickness ratio is recorded is used as the conversion table, conversion is completed by substituting the CT value of each pixel of the X-ray CT image 801 into the relational expression and using a return value as the water equivalent thickness ratio of the pixel (step S905). The conversion table may be a file or the like in which some CT values and corresponding water equivalent thickness ratios are discretely recorded, and may be converted into the water equivalent thickness ratio after processing such as linear interpolation is performed when a necessary CT value is not recorded in the file.

Referring back to step S704 of FIG. 7, subsequently, the target volume 209 is determined by the following procedure. First, the doctor extracts a contour of the tumor 211 (see FIG. 2) based on the pre-correction water equivalent thickness ratio distribution 905 or the X-ray CT image 801 displayed on the UI device 505. The contour of the target volume 209 is determined by adding a predetermined margin 210 to this contour. For example, when the margin 210 is uniformly defined as 10 mm within the target volume 209, the contour of the target volume 209 is set 10 mm outside the tumor 211 extracted by the doctor. The margin 210 may be uniform within the irradiation target 102 as in the present embodiment, or may be varied according to parameters such as a depth from a surface of the irradiation target 102.

Thus, the water equivalent thickness ratio distribution calculation on the first day (step S602) is completed. Referring back to FIG. 6, subsequently, the prescription creation program 508 of the treatment planning system 112 creates the prescription (step S603).

A procedure of the prescription creation will be described again with reference to FIG. 7.

First, the prescription creation program 508 reads the setting of the pre-correction water equivalent thickness ratio distribution 905 and the target volume 209 output from the water equivalent thickness ratio calculation program 507 (step S705).

Subsequently, the prescription creation program 508 sets the target dose for the target volume 209. The target dose is input by the doctor via the UI device 505 (step S706).

Subsequently, the prescription creation program 508 calculates the dose given to each calculation point designated in the target volume 209 by the beam 103 with which each spot is irradiated based on the pre-correction water equivalent thickness ratio distribution 905, and outputs the dose in the form of a matrix (hereinafter, referred to as a dose matrix) having as much elements as the product of the number of spots and the number of calculation points (step S707).

Subsequently, the prescription creation program 508 executes optimization calculation of the irradiation amount for giving the target dose based on the dose matrix, and determines the prescription, that is, the spot position and the irradiation amount of each beam 103 (step S708).

Subsequently, the prescription creation program 508 calculates a dose distribution formed by the prescription determined in the irradiation amount optimization calculation (step S709). The calculation result is confirmed by the doctor via the UI device 505. When the calculation result is approved by the doctor, the prescription is stored in the treatment planning system 112 and is transmitted to the overall control device 108 (step S710). Thus, the prescription creation (step S603) is completed. When the calculation result is not approved, the processing returns to step S706, and the target dose is reset.

Referring back to FIG. 6 again, subsequently, after the patient is placed on the treatment stand 107 and a position of the patient is adjusted so as to match a position at the time of capturing the X-ray CT image, the particle beam therapy system 101 starts irradiating the patient with the beam 103 (step S604). The irradiation is executed for each beam 103 adjusted based on the prescription input to the overall control device 108. The overall control device 108 controls the accelerator and beam transport system control device 109 and the irradiation nozzle control device 110 to change the spot position and the irradiation amount of each beam 103.

The range measurement device 111 measures the measured range 402 (see FIG. 4) for each beam 103 in parallel with the irradiation (step S605). Although FIG. 3 illustrates an example in which the range measurement is executed while the beams 103 are distinguished by reading the prescription from the overall control device 108, the measurement result may be distinguished into components of the beams 103 later while referring to an irradiation time of each beam 103 recorded in the overall control device 108 without distinguishing between the beams 103 at the time of range measurement.

When all the planned irradiations are completed, subsequently, the water equivalent thickness ratio correction program 509 starts the water equivalent thickness ratio correction (step S606). The procedure of the water equivalent thickness ratio correction will be described again with reference to FIG. 7.

First, the water equivalent thickness ratio correction program 509 reads the region 802 and the pre-correction water equivalent thickness ratio distribution 905 determined at the time of calculating the water equivalent thickness ratio and the prescription input at the time of creating the prescription (step S711). The execution of step S711 may not be executed after the completion of the irradiation and the range measurement (step S605), and may be executed in parallel with any step after the prescription creation in step S603 and before the determination of the water equivalent thickness ratio correction amount in step S713.

Subsequently, the water equivalent thickness ratio correction program 509 receives the measured range 402 of each beam 103 obtained in step S605 from the range measurement device 111 (step S712). The measured range 402 may be received for all the irradiated beams 103, or a statistic of the detection signal 401 used to determine the measured range 402 for the reliability determination of the measurement result may be acquired from the detector control device 305 and the range may be received only for the beam 103 of which the statistic exceeds a certain value.

Subsequently, the water equivalent thickness ratio correction amount is determined based on the prescription, the pre-correction water equivalent thickness ratio distribution 905, the region 802, and the measured range 402 (step S713). A method for determining the water equivalent thickness ratio correction amount will be described with reference to FIGS. 8 and 10.

First, an input amount used to determine the water equivalent thickness ratio correction amount is calculated. Before a specific calculation method is described, a principle of determining the water equivalent thickness ratio correction amount will be described with reference to FIG. 8 in order to show a necessary input amount.

When a difference between the range (hereinafter, referred to as a pre-correction range 803) estimated from the pre-correction water equivalent thickness ratio distribution 905 and the measured range 402 is caused by an error of the water equivalent thickness ratio distribution, it is considered that an error difference of a measured water equivalent thickness on a beam path coincides with a water equivalent thickness of a path (hereinafter, referred to as a difference path 804) between the pre-correction range 803 and the measured range 402. At this time, the following Equation (1) is satisfied.

[Math. 1]

$$\sum_i \delta l_{j,i} \cdot w_i = \sum_i l_{j,i} \cdot \delta w_i \qquad (1)$$

where, j and i are indexes representing the beam 103 and a pixel of the X-ray CT image 801, respectively, $\delta l$ represents a path length (hereinafter, referred to as a difference path length 805) in each pixel of the difference path 804, w represents a pre-correction water equivalent thickness ratio 806 of each pixel, l represents a measured path length (not illustrated) of each pixel, and δw represents an error of the water equivalent thickness ratio of each pixel. When δw satisfying Equation (1) is obtained, the water equivalent thickness ratio correction amount of each pixel is determined.

However, since the number of Equations (1) obtained by range measurement is limited to be equal to or less than the number of beams 103 used for treatment, the number of equations is often insufficient with respect to the number of variables δw, that is, the number of pixels. Thus, in the present embodiment, the difference path length 805 and the pre-correction water equivalent thickness ratio 806 of each pixel and a measured path length 807 of each region 802 are used as input amounts, and the water equivalent thickness ratio correction amount for each region 802 in which a plurality of pixels are collected is determined by the least squares method. That is, ow that minimizes the following Equation (2) is obtained.

[Math. 2]

$$f = \sum_j \left| \sum_i \delta l_{j,i} \cdot w_i - \sum_n l_{j,n} \cdot \delta w_n \right|^2 \quad (2)$$

Here, n is an index representing the region 802.

The principle of determining the water equivalent thickness ratio correction amount is described above. Next, a calculation procedure of each input amount will be described with reference to FIG. 8.

First, the measured path length 807 of each region 802 is calculated. Assuming that the beam 103 travels toward the spot position designated by the prescription, the path is determined by setting the position of the measured range 402 as an end of the beam 103 (solid arrow in FIG. 8). Since a path length for each region 802 is calculated from this path, the path length is set as the measured path length 807 and is stored in the treatment planning system 112. In the example of FIG. 8, since the path extends over three regions, measured route lengths (807A, 807B, and 807C) of the three regions are stored.

Subsequently, the difference path length 805 for each pixel and the pre-correction water equivalent thickness ratio 806 on the path are calculated. In order to calculate these input amounts, the pre-correction range 803 is required. The pre-correction range 803 is obtained from an integrated distance until a value obtained by determining the traveling direction of the beam 103 according to the prescription and integrating the pre-correction water equivalent thickness ratio along the direction matches a range in water. The difference path 804 is determined from the obtained pre-correction range 803 and measured range 402, and the difference path length 805 and the pre-correction water equivalent thickness ratio 806 in each pixel are calculated. In the example of FIG. 8, since the difference path 804 passes through only three pixels of a pixel 1 to a pixel 3, difference path lengths (805A, 805B, and 805C) and pre-correction water equivalent thickness ratios (806A, 806B, and 806C) at these three pixels may be calculated.

The treatment planning system 112 stores an amount obtained by summing the product of the difference path length 805 for each pixel and the pre-correction water equivalent thickness ratio 806 for all the pixels (corresponding to a water equivalent thickness on the difference path 804, hereinafter, referred to as difference water equivalent thickness).

As described above, all the input amounts used for determining the water equivalent thickness ratio correction amount are stored in the treatment planning system 112.

Referring back to step S713 in FIG. 7, subsequently, the water equivalent thickness ratio correction program 509 determines the water equivalent thickness ratio correction amount for each region 802 from the input amount stored in the treatment planning system 112 (step S714).

Figure 10:
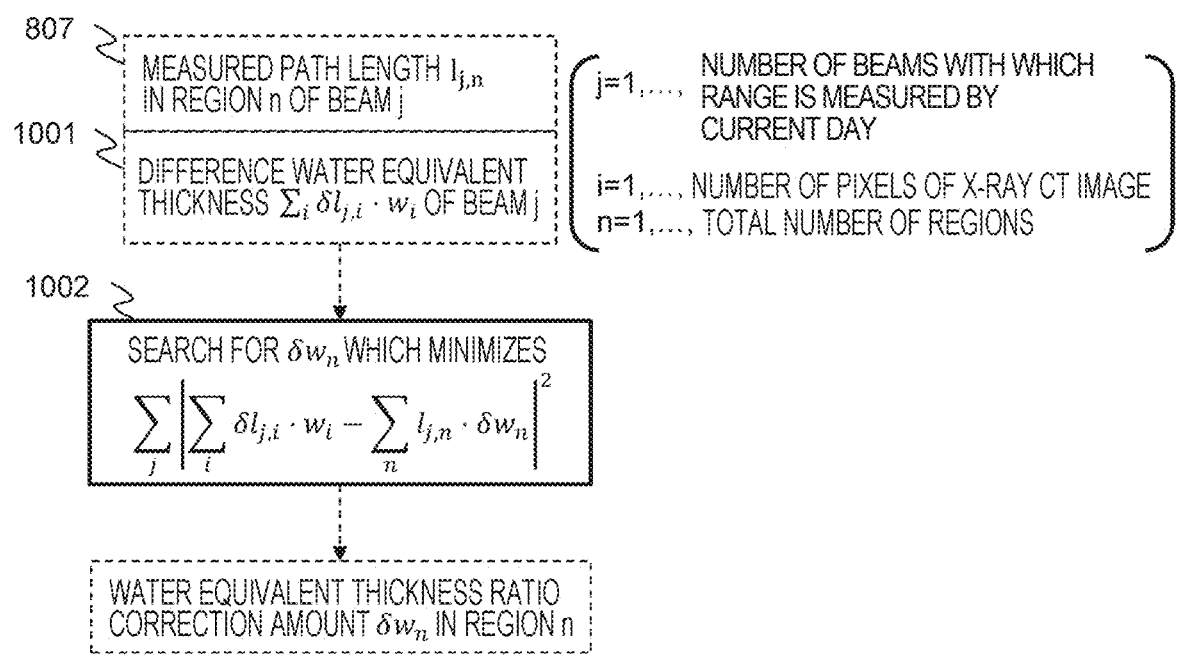
FIG. 10 is a diagram illustrating a procedure for determining the water equivalent thickness ratio correction amount by the treatment planning system according to the first embodiment.

A procedure for determining the water equivalent thickness ratio correction amount will be described with reference to FIG. 10. FIG. 10 is a diagram illustrating a procedure for determining the water equivalent thickness ratio correction amount using the least squares method.

First, the measured path length 807 for each region 802 of each beam 103 and a difference water equivalent thickness 1001 of each beam 103 stored in the treatment planning system 112 are called. Subsequently, a water equivalent thickness ratio correction amount 1002 which is an unknown amount is defined, and the water equivalent thickness ratio correction amount 1002 that minimizes Equation (2) is obtained. The water equivalent thickness ratio correction amount 1002 for each region 802 is determined by the above calculation. The determination method is not limited to the least squares method, and the water equivalent thickness ratio correction amount 1002 may be obtained by other methods.

Referring back to FIG. 7, a water equivalent thickness ratio calculation program 119 is read at the time of a next treatment by storing the water equivalent thickness ratio correction amount 1002 in the treatment planning system 112 (step S714). Thus, the water equivalent thickness ratio correction (step S606) is completed.

Referring back to FIG. 6, the treatment on the first day is ended by the completion of the water equivalent thickness ratio correction.

Subsequently, a treatment procedure on the second day and the subsequent days will be described again with reference to FIGS. 6 and 7. However, the description of the same procedure as on the first day will be simplified. In the present embodiment, the treatment procedure on the second day will be described as a representative, but the procedure is the same on the third day and the subsequent days.

After the start of treatment on the second day (step S601), the water equivalent thickness ratio calculation is executed (step S602). First, the region is divided based on the X-ray CT image captured again on the second day. Subsequently, the conversion to the water equivalent thickness ratio distribution and the determination of the target volume 209 are executed. At the time of the conversion into the water equivalent thickness ratio distribution, the pre-correction water equivalent thickness ratio distribution 905 is created in the same procedure as on the first day, and then the corrected water equivalent thickness ratio distribution 906 is created. A detailed procedure of the conversion is illustrated in FIG. 9 described above. The corrected water equivalent thickness ratio distribution 906 is a distribution obtained by adding the water equivalent thickness ratio correction amount 1002 determined on the previous day (referring to the first day in the treatment on the second day). The water equivalent thickness ratio correction amount 1002 stored on the previous day is read (step S903), and the conversion into the corrected water equivalent thickness ratio distribution 906 is completed by adding the water equivalent thickness ratio correction amount 1002 determined for each region 802 to the pre-correction water equivalent thickness ratio distribution 905 (step S904).

Referring back to step S704 of FIG. 7, subsequently, the target volume 209 (see FIG. 2) is determined. Similar to the first day, a range obtained by expanding the contour of the tumor 211 extracted by the doctor outward by a margin amount corrected based on the treatment result of the previous day is defined as the target volume 209. As a method for correcting the margin 210, in order to reflect the goodness of the fit of the water equivalent thickness ratio correction amount 1002 determined on the previous day, for example, there is a method for integrating a coefficient inversely proportional to a value obtained by substituting the determined water equivalent thickness ratio correction amount 1002 into δw of Equation (2) (a smaller value is taken as the fit is better) into a predetermined margin. Alternatively, a value proportional to the magnitude of the range error at the time of treatment on the previous day may be set, or may be reduced according to the number of pieces of information of the measured range 402 stored in the treatment planning system 112 in the treatment up to the previous day.

Referring back to FIG. 6, subsequently, the prescription is created (step S603). The procedure for creating the prescription is similar to the procedure on the first day. However, in order to reflect the effect of the water equivalent thickness ratio correction in the treatment plan, not the pre-correction water equivalent thickness ratio distribution 905 but the corrected water equivalent thickness ratio distribution 906 created on the second day is read and used for prescription creation.

After the prescription is created, the particle beam irradiation and the range measurement are executed in the same procedure as on the first day (step S604 and step S605), and subsequently the water equivalent thickness ratio correction is performed (step S606).

In the water equivalent thickness ratio correction, first, the difference water equivalent thickness 1001 of each beam 103 and the measured path length 807 for each region 802 are calculated from the prescription on the second day, the pre-correction water equivalent thickness ratio distribution 905, the measured range 402, and the region 802, and are stored in the treatment planning system 112. Subsequently, the water equivalent thickness ratio correction amount 1002 is determined by the same procedure as on the first day. However, not only the difference water equivalent thickness 1001 and the measured path length 807 on the second day, but also the difference water equivalent thickness 1001 and the measured path length 807 stored in the treatment planning system 112 by the previous day are the input amounts. This method is expected to achieve correction with higher accuracy than the first day.

After the water equivalent thickness ratio correction amount 1002 is determined, the same procedure as on the first day is followed, and the treatment on the second day is completed. The treatment procedure described above is repeated until the twenty-ninth day.

Next, a treatment procedure on the thirtieth day will be described with reference to FIG. 6. From the start of treatment (step S601) to the beam irradiation and the range measurement (step S605), the treatment is performed in the same procedure as from the second day to the twenty-ninth day. In the present embodiment, since the thirtieth day is the final treatment day, the water equivalent thickness ratio correction (step S606) is skipped, and the treatment on the thirtieth day is completed.

In the present embodiment, although the water equivalent thickness ratio correction is executed every day from the first day to the twenty-ninth day, it is not necessary to execute the water equivalent thickness ratio correction every day, and for example, the water equivalent thickness ratio correction may be executed every other day.

When the treatment on the thirtieth day is completed, the particle beam therapy in the present embodiment is ended.

Next, effects of the present embodiment will be described.

In the treatment planning system 112 according to the first embodiment described above, the water equivalent thickness ratio correction amount 1002 for each region 802 determined from the X-ray CT image 801 can be determined by using, as the input amounts, the measured path length 807 by the range measurement device 111 and the like. At the time of the treatment on the next day, when the X-ray CT image 801 is converted into the water equivalent thickness ratio distribution by dividing the region 802, the corrected water equivalent thickness ratio distribution 906 in which a difference in the correlation between the CT value and the water equivalent thickness ratio for each patient is considered can be acquired by adding the water equivalent thickness ratio correction amount 1002 calculated at the time of the treatment on the previous day to the pre-correction water equivalent thickness ratio 806 of each pixel. It is possible to suppress the range error caused by the patient dependence of the water equivalent thickness ratio by executing the treatment plan by using the corrected water equivalent thickness ratio distribution 906, and the treatment accuracy is improved. It is expected that it is possible to apply the particle beam therapy to pancreatic cancer or the like which has been difficult to apply a high dose in the particle beam therapy of the related art without performing the water equivalent thickness ratio correction by reducing the margin 210 in accordance with the improvement in treatment accuracy.

In the particle beam therapy system 101, the measured range 402 necessary for the water equivalent thickness ratio correction is measured in parallel with the beam irradiation. Since the water equivalent thickness ratio correction is automatically executed by the water equivalent thickness ratio correction program 509, the patient and the doctor are not restrained. Accordingly, the treatment time does not increase due to the water equivalent thickness ratio correction. Since the beam irradiation other than the treatment is not required, the device size does not become larger than a size of a general particle beam therapy system.

In the water equivalent thickness ratio correction using the range measurement of the beam irradiated at the time of treatment, since the number of pieces of information of the measured range 402 is limited to be equal to or less than the number of beams, the water equivalent thickness ratio cannot often be corrected for each pixel of the X-ray CT image 801. In order to correct the water equivalent thickness ratio, it is necessary to divide the X-ray CT image 801 into at least the regions 802 equal to or less than the number of pieces of information of the measured range 402, but in the method for uniformly determining the water equivalent thickness ratio for each region 802, the accuracy decreases as the difference in the water equivalent thickness ratio in the region 802 increases.

In the present embodiment, since the method for determining the water equivalent thickness ratio correction amount 1002 and adding the water equivalent thickness ratio to the water equivalent thickness ratio of each pixel before correction is used instead of determining the water equivalent thickness ratio itself for each region 802, even though the difference in the water equivalent thickness ratio in the region 802 is large, the correction accuracy does not decrease as long as the magnitude and the sign of the error are the same. That is, it is possible to improve high treatment accuracy from a limited number of pieces of information by determining the division of the region 802 and the water equivalent thickness ratio correction amount 1002 for each region 802.

Second Embodiment

Figure 11:
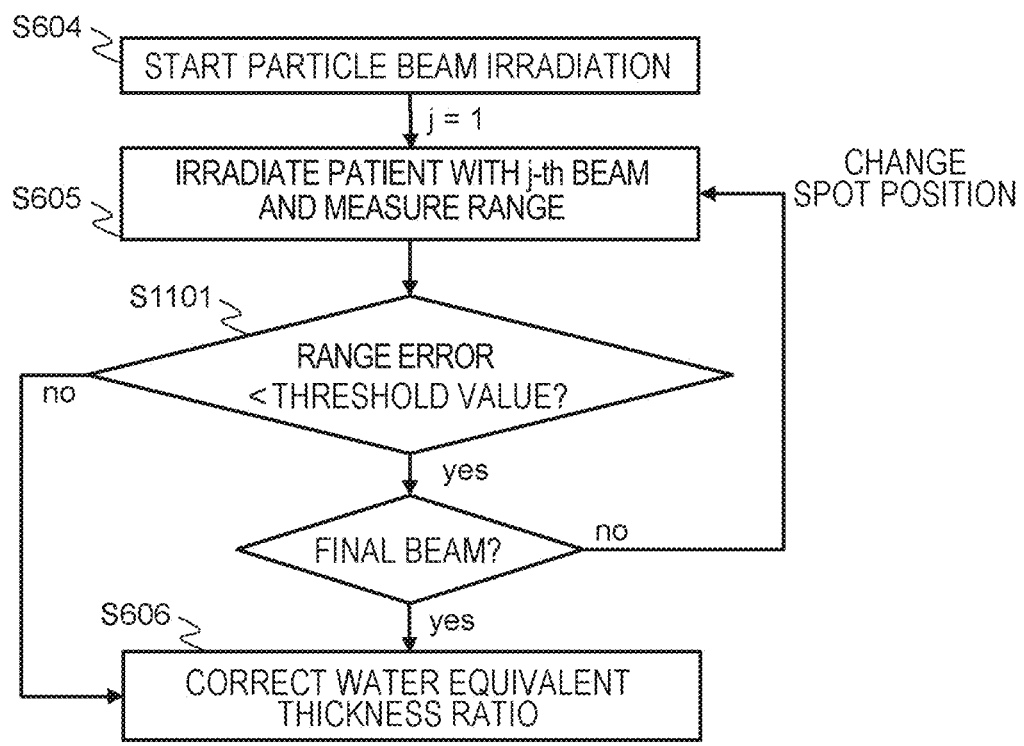
FIG. 11 is a flowchart illustrating a particle beam therapy by a particle beam therapy system according to a second embodiment.

A treatment planning system according to a second embodiment will be described with reference to FIG. 11. The same components as the components of the first embodiment are denoted by the same reference signs, and the description thereof will be omitted. FIG. 11 is a part of a flowchart illustrating a procedure of particle beam therapy according to the second embodiment.

In the present embodiment, an interlock based on the error determination after the range measurement of each beam 103 is added to the procedure of the particle beam therapy according to the first embodiment illustrated in FIG. 6 (step S1101). The range error is calculated after the irradiation and range measurement (step S605) of each beam 103, and when the range error exceeds a set threshold value (NO in S1101), the planned irradiation is stopped, and the water equivalent thickness ratio correction (step S606) is executed from the beam information irradiated until the stoppage, and the treatment cycle is ended. Subsequently, a new treatment cycle is started, the treatment plan is performed again based on the water equivalent thickness ratio correction amount 1002 and the irradiated dose obtained in step S606 of the previous treatment cycle, and the irradiation is resumed. Before the treatment plan, the X-ray CT image 801 of the patient may be captured again, or an image captured on the previous treatment may be used.

In order to determine the range error for each irradiation of each beam 103, it is necessary to calculate the range (hereinafter, referred to as a planned range) assumed by the prescription creation program 508 for each beam 103 before the start of the irradiation. In order to calculate the planned range, the pre-correction water equivalent thickness ratio distribution 905 may be replaced with the corrected water equivalent thickness ratio distribution 906 in the calculation procedure of the pre-correction range 803. The planned range is calculated by the water equivalent thickness ratio correction program 509 after the prescription is created and is stored in the treatment planning system 112.

The range error is determined by calculating the difference between the stored planned range and the measured range 402. The threshold value of the range error may be set by the doctor via the UI device 505 for each treatment, or may be automatically set by introducing a program for calculating a threshold value depending on the irradiation condition such as the spot position into the treatment planning system 112.

Next, effects of the present embodiment will be described.

In the treatment flow of the first embodiment, the prescription created at each treatment is not limited to the magnitude of the range error, and is executed up to the final spot. Accordingly, the irradiation is not stopped by the range measurement result, and the treatment time does not increase. However, particularly on the initial treatment day on which the water equivalent thickness ratio correction accuracy is not high, a range error on a scale larger than the margin 210 occurs, and a risk of damaging critical organs or the like cannot be excluded.

On the other hand, it is possible to suppress application of a large dose to the outside of the target volume 209 by adding the interlock after irradiation as in the second embodiment. Accordingly, as compared with the effect obtained in the first embodiment, there is a possibility that the treatment time increases, but it is expected to further improve the treatment accuracy, particularly to reduce the possibility of damaging the critical organs.

The present invention is not limited to the aforementioned embodiments, and includes various modification examples. The aforementioned embodiments are described in detail in order to facilitate easy understanding of the present invention, and are not limited to necessarily include all the described components. Some of the components of a certain embodiment can be substituted into the components of another embodiment, and the components of another embodiment can be added to the component of a certain embodiment. Additions, the components of another embodiment can be added, removed, and substituted to, from, and into some of the components of the aforementioned embodiments.

For example, although where the water equivalent thickness ratio is used for the physical quantity of the target to be corrected has been described, a stopping power ratio (a ratio between energy lost in a target tissue and energy lost in a reference tissue while the particle beam passes through a unit length) can be used instead of the water equivalent thickness ratio.

Although the target volume 209 obtained by adding the margin 210 to the tumor 211 has been described as the target for which the target dose is set, the target dose for critical organs around the target volume 209 may be additionally set.

Although the water equivalent thickness ratio correction is executed after the particle beam irradiation on each treatment day, the information such as the prescription and the measured range on each treatment day may be stored until the next day and may be executed before the calculation of the water equivalent thickness ratio on the next day.

A part or all of the aforementioned configurations, functions, processing units, and processing means may be realized by hardware by being designed with an integrated circuit, for example. Each of the aforementioned configurations and functions may be realized by software by interpreting and executing a program that realizes each function by the processor. Information of programs, tables, and files for achieving the functions can be stored in a recording device such as a memory, a hard disk, or an SSD, or a recording medium such as an IC card, an SD card, or a DVD.

Furthermore, control lines and information lines illustrated are considered to be necessary for the description, and not all the control lines and information lines in a product are necessarily illustrated. Almost all the configurations may be considered to be actually connected to each other.

REFERENCE SIGNS LIST 101 particle beam therapy system
102 irradiation target
103 beam
104 accelerator system
105 beam transport system
106 irradiation nozzle
107 treatment stand
108 overall control device
109 accelerator and beam transport system control device
110 irradiation nozzle control device
111 range measurement device
112 treatment planning system
209 target volume 210 margin
211 tumor
301 prompt gamma ray
302 collimator
303 slit
304 array type detector
305 detector control device
402 measured range
501 CPU
502 memory
503 storage device
504 communication interface
505 UI device
507 water equivalent thickness ratio calculation program
508 prescription creation program
509 water equivalent thickness ratio correction program
801 X-ray CT image
802A, 802B, 802C region
803 pre-correction range
804 difference path
805A, 805B, 805C difference path length
806A, 806B, 806C pre-correction water equivalent thickness ratio
807A, 807B, 807C measured path length
905 pre-correction water equivalent thickness ratio distribution
906 corrected water equivalent thickness ratio distribution
1001 difference water equivalent thickness
1002 water equivalent thickness ratio correction amount

The invention claimed is:

1. A treatment planning system which generates a treatment plan for irradiating an irradiation target with a particle beam, wherein
the treatment planning system is configured to:
calculate a correction amount of a first water equivalent thickness ratio of a first treatment plan created in advance,
calculate a second water equivalent thickness ratio distribution based on the correction amount and the first treatment plan, and
create a second treatment plan from the second water equivalent thickness ratio distribution,
wherein the correction amount is calculated based on a measured range of the particle beam measured according to irradiation of the particle beam based on the first treatment plan,
wherein an irradiation condition of the particle beam is included in the first treatment plan, and
wherein the correction amount is calculated based on the measured range and the irradiation condition.

2. The treatment planning system according to claim 1, wherein the measured range is a range based on a measurement result of a prompt gamma ray generated according to the irradiation of the particle beam.

3. The treatment planning system according to claim 1, wherein image data obtained by capturing the irradiation target is divided into a plurality of regions, and the correction amount for each region is calculated.

4. The treatment planning system according to claim 1, wherein a pre-correction range of the particle beam is obtained from the first treatment plan, and the correction amount is calculated based on the measured range and the pre-correction range.

5. The treatment planning system according to claim 4, wherein image data obtained by capturing the irradiation target and including a plurality of pixels is divided into a plurality of regions having the plurality of pixels, and the correction amount for each region is obtained by a least squares method by using, as inputs, a measured path length in the region obtained based on the measured range, a difference path length which is a difference between the measured range and the pre-correction range for each pixel constituting the region, and the water equivalent thickness ratio for each pixel constituting the region.

6. The treatment planning system according to claim 1, wherein, when a target dose of the particle beam as a target is irradiated multiple times, a plurality of the treatment plans are created for the irradiations performed multiple times, and the second treatment plan is performed to irradiate the irradiation target with the particle beam after the first treatment plan.

7. A particle beam therapy system comprising:
the treatment planning system according to claim 1;
an accelerator which accelerates a particle beam;
an irradiation device which irradiates an irradiation target with the particle beam accelerated by the accelerator;
a treatment planning system which generates a treatment plan for irradiating the irradiation target with the particle beam; and
a range measurement device which measures a range of the particle beam.

8. The particle beam therapy system according to claim 7, wherein
the treatment planning system obtains a pre-correction range of the particle beam from the first treatment plan,
the irradiation device stops irradiating the particle beam when a difference range which is a difference between the measured range and the pre-correction range exceeds a predetermined threshold value, and
the treatment planning system calculates the correction amount.

9. A treatment plan creation method by a treatment planning system which generates a treatment plan for irradiating an irradiation target with a particle beam, the method comprising:
calculating a correction amount of a first water equivalent thickness ratio of a first treatment plan created in advance;
calculating a second water equivalent thickness ratio distribution based on the correction amount and the first treatment plan; and
creating a second treatment plan from the second water equivalent thickness ratio distribution,
wherein the correction amount is calculated based on a measured range of the particle beam measured according to irradiation of the particle beam based on the first treatment plan,
wherein an irradiation condition of the particle beam is included in the first treatment plan, and
wherein the correction amount is calculated based on the measured range and the irradiation condition.

10. A non-transitory computer readable storage medium storing thereon a computer program causing a computer, which generates a treatment plan for irradiating a target with a particle beam, to execute:
a function of calculating a correction amount of a first water equivalent thickness ratio of a first treatment plan created in advance;
a function of calculating a second water equivalent thickness ratio distribution based on the correction amount and the first treatment plan; and
a function of creating a second treatment plan from the second water equivalent thickness ratio distribution, wherein the correction amount is calculated based on a measured range of the particle beam measured according to irradiation of the particle beam based on the first treatment plan,
wherein an irradiation condition of the particle beam is included in the first treatment plan, and
wherein the correction amount is calculated based on the measured range and the irradiation condition.

* * * * *